(12) United States Patent
Cohen

(10) Patent No.: US 7,482,029 B2
(45) Date of Patent: Jan. 27, 2009

(54) COMPOSITION FOR TREATMENT OF MENOPAUSE

(75) Inventor: Isaac Cohen, Piedmont, CA (US)

(73) Assignee: BioNovo, Inc., Emeryville, CA (US)

( * ) Notice: Subject to any disclaimer, the term of this patent is extended or adjusted under 35 U.S.C. 154(b) by 155 days.

(21) Appl. No.: 11/277,811

(22) Filed: Mar. 29, 2006

(65) Prior Publication Data

US 2006/0222721 A1 Oct. 5, 2006

Related U.S. Application Data

(60) Provisional application No. 60/667,887, filed on Apr. 1, 2005.

(51) Int. Cl.
*A01N 65/00* (2006.01)
(52) U.S. Cl. .................... 424/725; 514/899
(58) Field of Classification Search ................. 424/725; 514/899
See application file for complete search history.

(56) References Cited

U.S. PATENT DOCUMENTS

| 6,238,707 | B1 * | 5/2001 | Chun |
| 2003/0170292 | A1 * | 9/2003 | Yong et al. |
| 2003/0190375 | A1 * | 10/2003 | Erdelmeier et al. |
| 2005/0196409 | A1 | 9/2005 | Dao et al. |

FOREIGN PATENT DOCUMENTS

| JP | 2001122871 A | * | 5/2001 |
| JP | 2002029980 A | * | 1/2002 |
| JP | 2004155779 A | * | 6/2004 |
| WO | WO-2005-044182 A2 | | 5/2005 |

OTHER PUBLICATIONS

Bensky, D et al., Chinese Herbal Medicine: Formulas & Strategies (1990), Eastland Press, Inc. Seattle, Washington, pp. 117, 224, 379, 380, 383 and 384.*
Lee, T-K et al. International Immunology (2004); 4: 447-454. Inhibitory effects of Scutellaria barbata D. Don on human uterine leiomyomal smooth muscle cell proliferation through cell cycle analysis.*
Liu, C-W et al. Pharm Res (1995; 12(Suppl): s126. Estrogen receptor assays of Scutellariae Barbatae Herba, Lithospermix Radix and Oldenlandiae Herba.*
Albert, A et al. Phytomedicine (2002): 9:85-92. Efficacy and safety o phytoestrogen preparation derived from Glycine max (L.) Merr in climacteric symptomatology: a multicentric, open, prospective and non-randomized trial.*
Duffy R et al. Pharmacology Biochemistry and Behavior (2003); 75(3): 721-729. Improved cognitive function in postmenopausal women after 12 weeks of consumption of a soya extract containing isoflavones.*
Suthar, AC et al. Indian Journal of Experimental Biology (2001); 39(6): 520-525. Pharmacological activities of genistein, an isoflavone from soy (Glycine max): Part II- Anti-cholesterol activity, effects on osteoporosis & menopausal symptoms.*
Wang, P et al. Mechanisms of Ageing and Development (2003); HDTIC-1 and HDTIC-2, two components extracted from Astragali Radix, delay replicative senescence of human diploid fiboblasts.*
Hsu, H-Y et al. Oriental Materia Medica: A Concise Guide (1986); Keats Publishing Inc., USA, pp. 119, 120, 144, 145, 272, 273, 524 and 525.*
Xiao-fan, Z et al. Chinese Medicna Teas: Simple, Proven Folk Formulas for Common Disease Promoting Health (Aug. 2004, Blue Poppy Press,Third Printing USA; pp. 122, 123, 252, 253-255 and 263.*
Lu, HC. Chinese Herbs with Common Foods: Recipes for Health and Healing (1997), Japan; Kodansha International Inc., pp. 94, 115,119, and 120.*
Baek, J. et al., "Effects of Methyl Chloride (MC) Fraction Isolated from Scutellaria Barbata on Apoptosis of a Human Lymphoma Cell Line (U937) Cells," Blood 100(11):279B, Abstract 4650 (2002).
Campbell, M.J. et al., "Antiproliferative Activity of Chinese Medicinal Herbs on Breast Cancer Cells In Vitro," Anticancer Research 22:3843-3852 (2002).
Chui, C.H. et al., "Anti-cancer potential of traditional Chinese herbal medicines and microbial fermentation products," Minerva Biotech 17:183-191 (2005).
Chui, C.H. et al., "Activities of fresh juice of Scutellaria Barbata and warmed water extract of Radix Sophorae Tonkinensis on anti-proliferation and apoptosis of human cancer cell lines," Intl J Mol Med 16:337-341 (2005).
Ducki, S. et al., "Isolation of E-1-(4'-Hydroxyphenyl)-but-1-en-3-one from Scutellaria barbata," Planta Medica 62:185-186 (1996).
Fong et al., "Poster Presentation," Proceedings of the American Association for Cancer Research 95th Annual Meeting, 2007 AACR Annual Meeting, Apr. 14-18, 2007, Los Angeles, Abstract 4837.
GOH, D. et al., "Inhibitory Effects of a Chemically Standardized Extract from Scutellaria barbata in Human Colon Cancer Cell Lines, LoVo," J Agric. Food Chem. 53:8197-8204 (2005).
Kim, D. et al., "Regulation of IGF-1 production and proliferation of human leiomyomal smooth muscle cells by Scutellari barbata D. Don in vitro: isolation of flavonoids of apigenin and luteolon as acting compounds," Toxicology and Applied Pharmacology 205:213-224 (2005).
Kummalue, T., "Molecular Mechanism of Herbs in Human Lung Cancer Cells," J. Med. Assoc.Thai. 88(11):1725-1734 (2005).
Lawrence, N.J. et al., "The Chemistry and Biology of Antimitotic Chalcones and Related Enone Systems," Current Pharmaceutical Design 11:1670-1693 (2005).

(Continued)

*Primary Examiner*—Michele Flood
(74) *Attorney, Agent, or Firm*—Wilson Sonsini Goodrich & Rosati

(57) ABSTRACT

A method of using an herbal extract of a mixture of: Herba *Scutellaria barbata*, Radix *Sophora subprostratae*, Radix *Anemarrhena*, Semen *Glycine sojae*, Radix *Glycyrrhiza*, Rhizoma *Rhei*, Fructus *Tritici levis*, Radix *Astragali*, Radix *Rehmania*, Fructus *Ligustri lucidi*, Semen *Zyziphi spinosa*, Plumula *Nelumbinis*, *Poria cocos*, Rhizoma *Alismatis*, Cortex *Moutan radicis*, Fructus *Corni*, Radix *Achyranthis*, Concha *Ostrea*, Radix *Aspargi*, Radix *Pueraria*, Radix *Atractylodis macrocephala* and Herba *Epimedium*, for the treatment of hot flashes associated with menopause is disclosed herein.

7 Claims, 6 Drawing Sheets

OTHER PUBLICATIONS

Lee, T.K. et al., "Scutellaria barbata D.Don induces c-fos gene expression in human uterine leiomyomal cells by activating β2-adrenergic receptors," Int. J. Gynecol. Cancer 14:526-531 (2004).

McHenry, A.M. et al., "Modulation of apoptosis in LNCaPcells by the Chinese medicinal herb Scutellaria barbata," AACR Meeting Abstracts Online , Abstract 721, Proc. Amer. Assoc. Cancer Res. 45 (2004) http://.www.aacrmeetingabstacts.org/cpi/content/abstract/2004/1/167.

Powell, C.B. et al., "Aqueous extract of herba Scutellaria barbatae, a chinese herb used for ovarian cancer, induces apoptosis of ovarian cancer cell lines," Gynecologic Oncology 91:332-340 (2003).

Rugo, H. et al., "Phase I trial and antitumor effects of BZL101 for patients with advanced breast cancer," Breast Cancer Res Treat 105(1):17-28 (2007) DOI 10.1007/s10549-006-9430-6, Springer Science-Business Media B.V. 2006.

Shoemaker, M. et al., "In Vitro Anticancer Activity of Twelve Chinese Medicinal Herbs," Phytotherapy Research 19:649-651 (2005).

Song, H.Z. et al., "In Vitro Study of the Chemopreventive Effects of Chinese Herbs against Hepatocarcinogenesis," J. Clin. Biochem. Nutri. 35:1-5 (2004).

Tagliaferri, M. et al., "A phase I trial of scutellaria barbata (BZL101) for metastatic breast cancer," Abstract 1079, Breast Cancer Research and Treatment 94 ( Suppl. 1 ): p S66 2005 2005.

Tan, B.K.H. et al., "Traditional Chinese Medicines in Breast Cancer: Clinical and Experimental Data," Abstract 356, Intl J Mol Med 12(Supp 1):S68 (2003).

Voskoglou-Nomikos et al., "Clinical Predictive Value of the in Vitro Cell Line, Human Xenograft, and Mouse Allograft Preclinical Cancer Models," Clin. Cancer Res. 9:4227-4239 (2003).

Wong, B.Y. et al., "Chinese Medicinal Herb Scutellaria barbata Modulates Apoptosis in TRAMP-C1 Prostate Cancer Cells and Tumor Development in TRAMP Mice," American Assoication for Cancer Research Conference on Frontiers in Cancer Prevention Research, Oct. 26-30, 2003, Phoenix, AZ, Cancer Epidemiology, Biomarkers & Prevention 12(Supp):1326s, Poster Session B, Nov. 2003, Poster B190.

Wong, B.Y. et al., "Modulation of Apoptosis and Cell Survival in Human Prostate Cancer Cells by the Chinese Medicinal Herb Scutellaria barbata," American Association for Cancer Research Conference on Frontiers in Cancer Prevention Research, Oct. 30-Nov. 2, 2005, Baltimore , MD Poster Session B, Biomarkers and Early Detection:Health Disparities, Cell,Molecular and Tumor Biology: Cell Death, Poster B21, p. 104.

Yin, X. et al., "Anticancer activity and mechanism of Scutellaria barbata extract on human lung cancer cell line A549," Life Sciences 75:2233-2244 (2004).

Yu, H. et al., "Anti-tumor effect of Chinese herbal medicines "Scutellaria barbata and Oldenlandia diffusa" on cancer cell lines and C3H-AVy mouse with spontaneous hepatocellular carcinoma," J Traditional Medicines 17(4):165-169 (2000).

Zhu, F. et al., "Regulative Effect of Traditional Chinese Medicine on Gene-expression Related to Precancerous Lesion of Gastric Cancer," Chinese J. Integrative Med. 11(1):76-80 (2005).

PCT/US06/044224 Search Report dated Nov. 7, 2007.

* cited by examiner

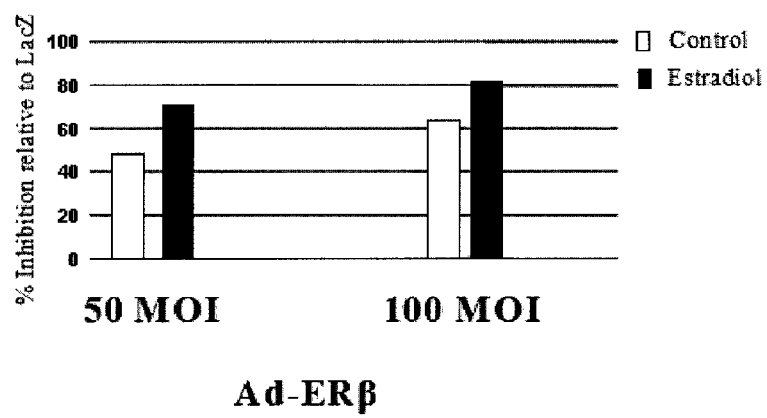
Figure 4. ERβ effects on MCF-7 cell proliferation with and without estradiol.

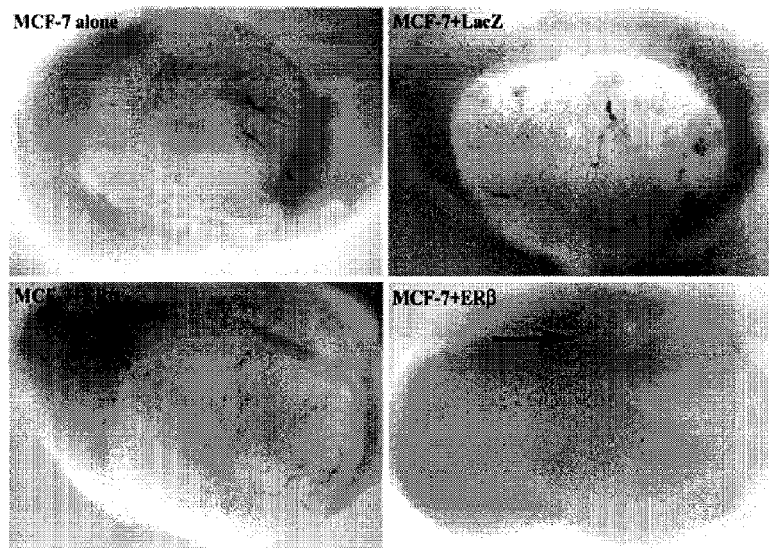
Figure 5. In vivo effects of ERα and ERβ on in vivo cell proliferation
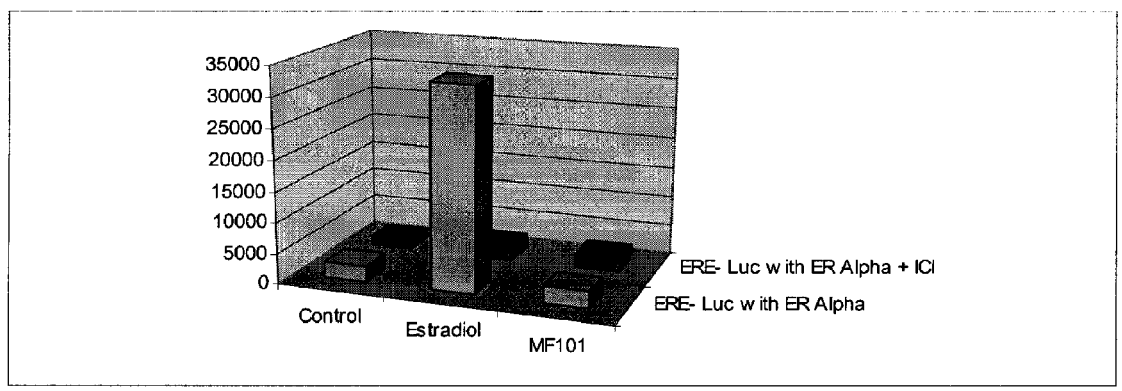
Figure 6. Estradiol, Not MF101, Activates ERα in vitro

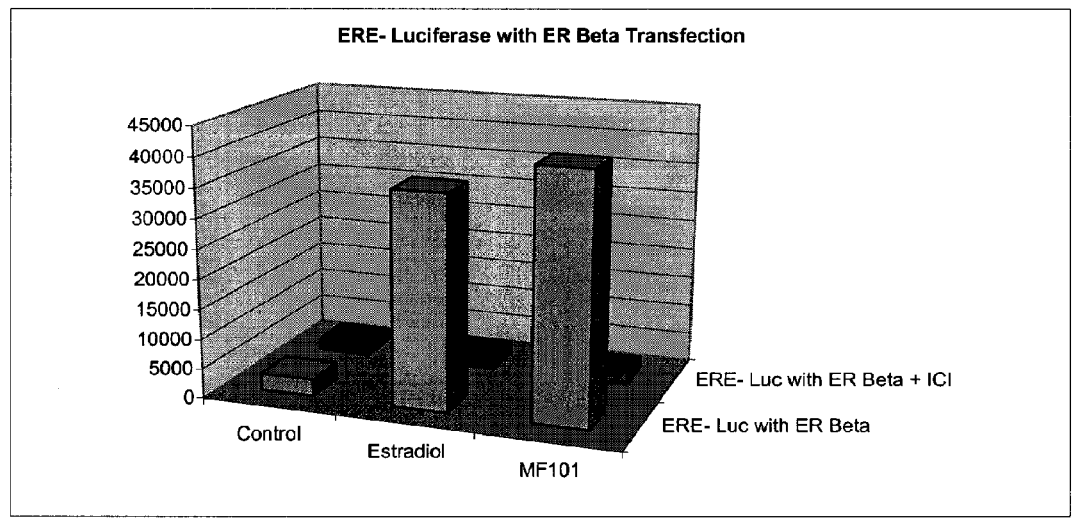
Figure 7. MF101 Selectively Interacts with ERβ
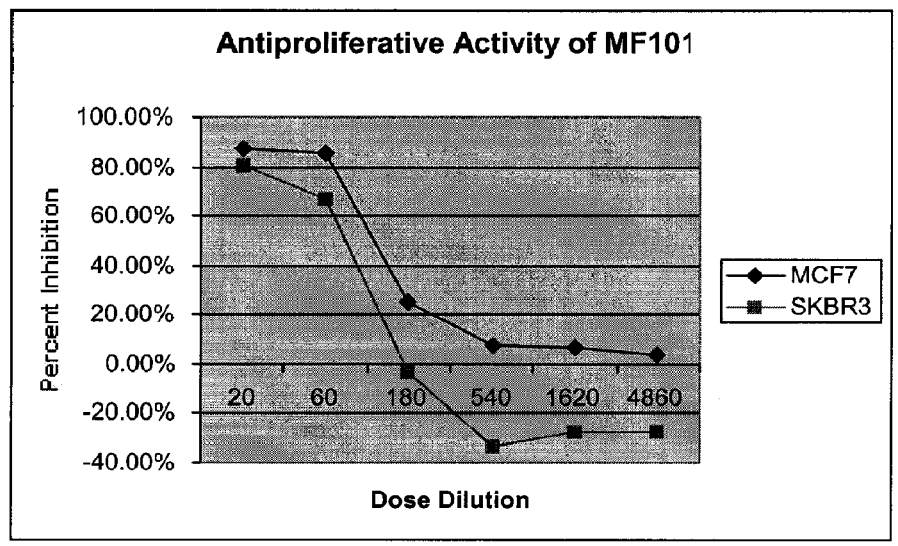
Figure 8. Anti-proliferative Effect of MF101

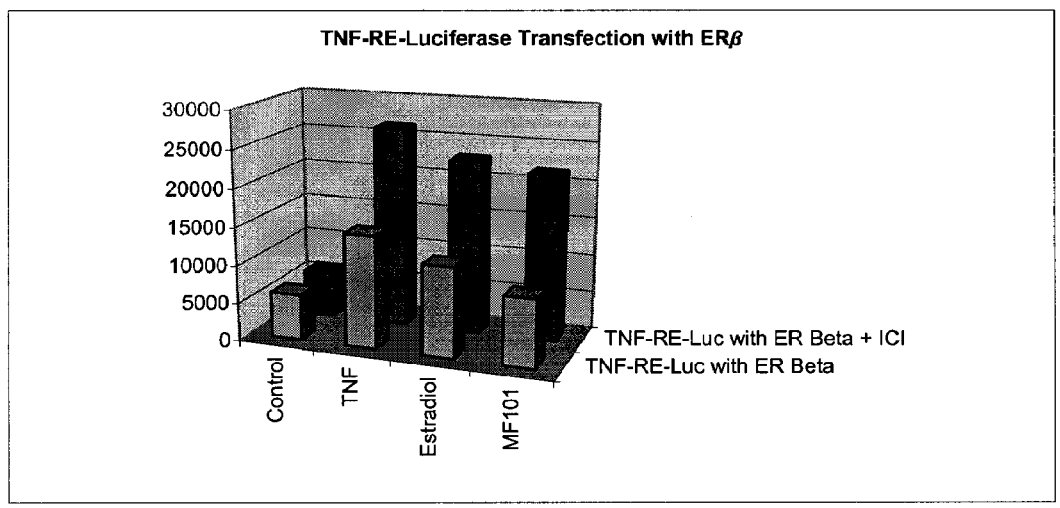
Figure 9. MF101 Can Protect Bone Cells from the Activity of TNFβ

COMPOSITION FOR TREATMENT OF MENOPAUSE

CROSS REFERENCE

This application claims the benefit under 35 U.S.C. § 119(e) of U.S. Provisional Application No. 60/667,887, filed Apr. 1, 2005, which is incorporated herein by reference in its entirety.

BACKGROUND OF THE INVENTION

Menopause is that period after the cessation of normal ovulation cycles, during which normal menstruation ceases. A decrease in estradiol ($E_2$) production accompanies menopause, as the ovaries cease manufacture of $E_2$. This decrease in $E_2$ production results in a shift in hormone balance in the body, which often gives rise to a variety of symptoms associated with menopause.

Peri-menopause, which is also known as pre-menopause or the climacteric, is that period prior to menopause during which normal ovulation cycles gradually give way to cessation of menses. As the ovulatory cycles lengthen and become more irregular, the level of $E_2$ may initially increase, but will eventually drop with the onset of menopause. Menopausal symptoms often accompany the drop in $E_2$ levels.

The symptoms of peri-menopause, menopause and post-menopause include physical symptoms such as hot flashes and sweating secondary to vasomotor instability. Additionally, psychological and emotional symptoms may accompany onset of climacteric, such as fatigue, irritability, insomnia, inability to concentrate, depression, memory loss, headache, anxiety and nervousness. Additional symptoms can include intermittent dizziness, paresthesias, palpitations and tachycardia as well as nausea, constipation, diarrhea, arthralgia, myalgia, cold hands and feet and weight gain. In addition, changes to the genitals, urinary incontinence, vaginal dryness, loss of pelvic muscle tone, increased risk of cardiovascular disease and osteoporosis increase with onset of menopause.

Hot flashes are prevalent in, and bothersome to, many peri-menopausal, menopausal and postmenopausal women. For decades hormone replacement therapy with estrogens has been the standard treatment for hot flashes, but many women have abandoned hormone therapy (HT) due to concerns about potential adverse effects, particularly breast cancer. Several recent studies, in particular the Women's Health Initiative (WHI), have found that HT increases the risk of breast cancer. The observation that the selective estrogen receptor modulators ("SERMs") raloxifene and tamoxifen prevent estrogen receptor (ER) positive breast cancer provides additional evidence that estrogens promote breast cancer.

There is thus a need for therapeutic compositions and methods for the treatment of menopause, especially menopausal symptoms such as hot flashes, which do not increase the risk of breast cancer. The present invention satisfies this need and provides related advantages as well.

SUMMARY

The present invention provides a composition for the treatment of menopause. The composition is a mixture of herbs, an extract of a mixture of herbs or a mixture of herbal extracts. The mixture of herbs comprises Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis*, Poria *Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. The composition activates the estrogen response element (ERE) through estrogen receptor beta (ERβ), but not estrogen receptor alpha (ERα) in an in vitro assay.

The invention also provides a method of treating menopause. The method comprises administering to a subject an amount of the above-mentioned composition sufficient to treat menopause. In some embodiments, treatment of menopause includes reducing the severity, frequency or severity and frequency of a menopausal symptom.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which.

FIG. 4 is a bar graph depicting the effect of ERβ on MCF cell proliferation with and without estradiol.

FIG. 5 depicts the effects of ERα and ERβ on in vivo cell proliferation.

FIG. 6 is a three dimensional bar graph showing that estradiol, but not MF-101, activates ERα in vivo.

FIG. 7 is a three dimensional bar graph showing that MF-101 selectively interacts with ERβ.

FIG. 8 is a line graph showing the anti-proliferative effect of MF-101.

FIG. 9 is a three dimensional bar graph showing that MF-101 protects bone cells from TNFβ activity.

DETAILED DESCRIPTION OF THE INVENTION

Figure 1A:
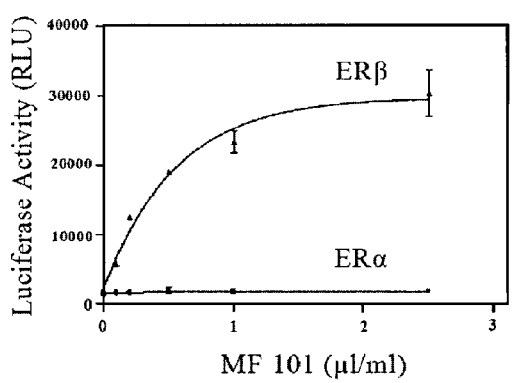
FIG. 1A is a line graph comparing the activity of MF101 on ERβ and ERα expressing cells. MF101 produced a dose-dependent activation of ERE-tk-Luc with ERβ, but no activation was observed with ERα.

Many women are eagerly awaiting safe and effective alternatives to estrogens used in HT for menopausal symptoms after the results of the Women's Health Initiative trial, which showed that the risks of HT exceed the benefits (Ettinger, B., Grady, D., Tosteson, A. N., Pressman, A. & Macer, J. L., "Effect of the Women's Health Initiative on women's decisions to discontinue postmenopausal hormone therapy," *Obstet. Gynecol.* 102, 1225-32 (2003)). In the meantime a recent survey reported that 79% of peri- and post-menopausal women are using botanical dietary supplements (BDS) (Mahady, G. B., Parrot, J., Lee, C., Yun, G. S. & Dan, A. Botanical dietary supplement use in peri- and postmenopausal women. *Menopause* 10, 65-72 (2003)). Despite the widespread use of BDSs, the mechanism of action, efficacy and safety of botanicals have not been rigorously examined. The present invention provides an herbal formula that contains Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis, Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. In some embodiments, the extract is an extract of a significant amount of each of the herbs: Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis, Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. An exemplary embodiment of the invention is MF101, which is described in more detail below. Although many of the herbs contained in MF101 have been used in traditional Chinese herbal concoctions for the treatment of climacteric symptoms, no previous study has every confirmed the efficacy of the mixture for treatment of menopause. A composition of the invention has ERβ-selective estrogen receptor activity, and thus is well-suited for the clinical treatment of menopause, especially to treat menopausal symptoms such as hot flashes.

The invention provides compositions and methods for the treatment of menopause, especially menopausal symptoms such as hot flashes. The compositions of the invention are herbal mixtures, extracts of herbal mixtures and mixtures of herbal extracts. The invention compositions additionally activate the estrogen response element (ERE) with estrogen receptor beta (ERβ) but not estrogen receptor alpha (ERα) in U2OS osteosarcoma cell assays. As the compositions activate the ERE through interaction with ERβ but not ERα, only the latter of which is associated with adverse effects of estrogen HT, the invention compositions and methods represent an alternative to estrogen hormone therapy and are less likely to give rise to conditions identified in the WHI as being associated with estrogen supplementation, such as increased risk of breast cancer.

In the context of the present invention "menopause" includes peri-menopause, menopause and post-menopause, and in particular, symptoms that are caused or exacerbated by the decreased levels of estradiol ($E_2$) that attend peri-menopause, menopause and post-menopause. Thus, in the context of the present invention, "treatment of menopause" means treatment of menopausal symptoms. Exemplary menopausal symptoms include hot flashes, sweating secondary to vasomotor instability, psychological and emotional symptoms such as fatigue, irritability, insomnia, inability to concentrate, depression, memory loss, headache, anxiety, nervousness, intermittent dizziness, paresthesias, palpitations, tachycardia, nausea, constipation, diarrhea, arthralgia, myalgia, cold hands and feet, weight gain, urinary incontinence, vaginal dryness, loss of pelvic muscle tone, increased risk of cardiovascular disease and osteoporosis.

Thus, "treatment of menopause" means the alleviation, palliation or prevention of one or more symptoms associated with peri-menopause, menopause or post-menopause, and includes reduction in the severity or frequency of at least one menopausal symptom. The use of "or" as used herein is intended to be conjunctive unless otherwise specified. Thus, treatment also includes reduction of both the severity and frequency of at least one menopausal symptom. In the sense that reduction of the frequency and severity of a symptom may be complete, treatment may also include prevention of the symptom. In this regard, it is noted that treatment of menopause does not include prevention of the natural cessation of menses in the adult female human, although it does include reduction to undetectable levels the frequency and severity of at least one symptom associated with menopause.

In the context of the present invention, "menopausal subject" and its verbal variants refers to an adult female, especially an adult female human, who has once attained menarche and who is experiencing peri-menopause, menopause or post-menopause. One of skill in the art of gynecology will be able to identify the diagnostic characteristics of the onset of menopause and identify a subject as being a "menopausal subject" by art-recognized clinical methods.

Compositions according to the present invention include herbal mixtures comprising each of the following herbs: Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis, Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. In some embodiments, the herbal mixture comprises a significant amount of each of the foregoing herbs. In this context a significant amount means an amount greater than about 0.1% by weight, for example greater than about 0.5%, and more particularly greater than about 1% by weight of the mass of all herbal matter in the herbal mixture. Compositions according to the invention also include extracts of the foregoing herbal mixtures. The methods of making such extracts are described in detail below.

In some embodiments of the invention, the herbal mixtures comprise, consist essentially of, or consist of a mixture of the herbs in approximately or precisely the proportions listed in Table 2.

TABLE 2

| Herbal Ingredient | Proportion (percent by weight of total composition) |
|---|---|
| Herba Scutellaria Barbata | 5-16% |
| Radix Sophora Subprostratae | 5-16% |
| Radix Anamarrhena | 2-6% |
| Semen Glycine Sojae | 3.5-10.5% |
| Radix Glycyrrhiza | 1.5-4.5% |
| Rhizoma Rhei | 1.5-4.5% |
| Fructus Tritici Levis | 2.5-7.5% |
| Radix Astragali | 2-6% |
| Radix Rehmania | 2-6% |
| Fructus Ligustri Lucidi | 2.5-7.5% |
| Semen Zyziphi Spinozae | 1.8-5.4% |
| Plumula Nelumbinis | 1.8-5.4% |
| Poria Cocos | 1.8-5.4% |
| Rhizoma Alismatis | 1.8-5.4% |
| Cortex Moutan Radicis | 1.5-4.5% |
| Fructus Corni | 1.8-5.4% |
| Radix Achyranthis | 1.8-5.4% |
| Concha Ostrea | 2-6% |
| Radix Asparagi | 2-6% |
| Radix Pueraria | 1.8-5.4% |
| Radix Atractylodis Macrocephala | 1.8-5.4% |
| Herba Epimedi | 1.5-4.5% |

In some embodiments, the herbal mixtures of the invention comprise, consist essentially of or consist of the herbal ingredients in the approximate or precise proportions set forth in Table 3.

TABLE 3

| Herbal Ingredient | Proportion (percent by weight of total composition) |
|---|---|
| Herba Scutellaria Barbata | 7.5-12.5% |
| Radix Sophora Subprostratae | 7.5-12.5% |
| Radix Anamarrhena | 3-5% |
| Semen Glycine Sojae | 5-9% |
| Radix Glycyrrhiza | 2-4% |
| Rhizoma Rhei | 2-4% |
| Fructus Tritici Levis | 4-7% |
| Radix Astragali | 3-5% |
| Radix Rehmania | 3-5% |
| Fructus Ligustri Lucidi | 4-7% |
| Semen Zyziphi Spinozae | 2.7-4.5% |
| Plumula Nelumbinis | 2.7-4.5% |
| Poria Cocos | 2.7-4.5% |
| Rhizoma Alismatis | 2.7-4.5% |
| Cortex Moutan Radicis | 2-4% |
| Fructus Corni | 2.7-4.5% |
| Radix Achyranthis | 2.7-4.5% |
| Concha Ostrea | 3-5% |
| Radix Asparagi | 3-5% |
| Radix Pueraria | 2.7-4.5% |
| Radix Atractylodis Macrocephala | 2.7-4.5% |
| Herba Epimedi | 2-4% |

In particular embodiments, the invention provides herbal mixtures comprising, consisting essentially of or consisting of the herbal ingredients in approximately or precisely the proportions set forth in Table 4.

TABLE 4

| Herbal extract: | Proportion of the mixture of extracts |
|---|---|
| Herba Scutellaria Barbata | 7.2% |
| Radix Sophora Subprostratae | 5.6% |
| Radix Anamarrhena | 11.6% |
| Semen Glycine Sojae | 2.7% |
| Radix Glycyrrhiza | 5.1% |
| Rhizoma Rhei | 4.7% |
| Fructus Tritici Levis | 3.6% |
| Radix Astragali | 4.9% |
| Radix Rehmania | 14.9% |
| Fructus Ligustri Lucidi | 6.1% |
| Semen Zyziphi Spinozae | 2.2% |
| Plumula Nelumbinis | 4.0% |
| Poria Cocos | 0.3% |
| Rhizoma Alismatis | 1.6% |
| Cortex Moutan Radicis | 2.1% |
| Fructus Corni | 3.3% |
| Radix Achyranthis | 10.0% |
| Concha Ostrea | 1.9% |
| Radix Asparagi | 0.1% |
| Radix Pueraria | 2.0% |
| Radix Atractylodis Macrocephala | 4.6% |
| Herba Epimedi | 1.5% |

The terms comprising, consisting essentially of and consisting of have the meanings generally accepted in the art. The term approximate and its variants mean that the tolerance for a particular value in the respective table is in the range of +/−10% of the value given. Thus, for example, a value that is approximately 10% would be (10+/−1)%: that is in the range of 9-11%. The term precise and its variants mean that the tolerance for a particular value in the respective table is in the range of +/−1% of the value given. Thus, for example, a value that is precisely 10.0% would be (10+/−0.1)%: that is in the range of 9.9 to 10.1%. In some embodiments, the proportions given in Tables 1-3 are approximate, whereas in other embodiments the proportions are precise.

In some embodiments, the present invention provides a composition that is an extract of an herbal mixture as described above. In some embodiments, the extract of the invention is an extract of an herbal mixture comprising the herbs: Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis*, *Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. In some embodiments, the extract is an extract of a significant amount of each of the herbs: Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis*, *Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. In other embodiments, the extract is an extract of an herbal mixture set forth in Table 2. In further embodiments, the extract is an extract of an herbal mixture set forth in Table 3. In still further embodiments, the extract is an extract of an herbal mixture set forth in Table 4.

In some embodiments of the invention, the composition is a reduced or dehydrated extract of a herbal mixture. In some embodiments, the composition is a dehydrated or reduced extract of an herbal mixture comprising the herbs: Herba

*Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis, Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. In some embodiments, the composition is a reduced or dehydrated extract of a significant amount of each of the herbs: Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis, Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*. In other embodiments, the composition is a reduced or dehydrated extract of an herbal mixture set forth in Table 2 or Table 3 or Table 4.

In some embodiments, the present invention provides a composition that is a combination of one or more of the foregoing extracts or reduced or dehydrated extracts with one or more suitable diluents, flavoring agents, excipients or other additives. Suitable diluents include water, for example deionized water, water for injection (WFI), filtered water, etc. Other suitable diluents include fruit juices, teas, milk, milk of magnesia, etc. Suitable flavorings include fruit flavorings, wintergreen, peppermint, spearmint, cinnamon, etc. Other suitable additives including food colorings and ethanol. In some embodiments, the composition comprises a dehydrated extract combined with one or more diluents, flavoring agents or other additives. In other embodiments, the composition comprises a reduced extract in combination with one or more diluents, flavoring agents or other additives. In some particular embodiments, the dehydrated extract is a dehydrated extract of one of the mixtures set forth in Table 2, Table 3 or Table 4. In other particular embodiments, reduced extract is a reduced extract of one of the herbal mixtures set forth in Table 2, Table 3 or Table 4.

The compositions according to the invention include mixtures of the herbs: Herba *Scutellaria Barbata*, Radix *Sophora Subprostratae*, Radix *Anamarrhena*, Semen *Glycine Sojae*, Radix *Glycyrrhiza*, Rhizoma *Rhei*, Fructus *Tritici Levis*, Radix *Astragali*, Radix *Rehmania*, Fructus *Ligustri Lucidi*, Semen *Zyziphi Spinozae*, Plumula *Nelumbinis, Poria Cocos*, Rhizoma *Alismatis*, Cortex *Moutan Radicis*, Fructus *Corni*, Radix *Achyranthis*, Concha *Ostrea*, Radix *Asparagi* and Radix *Pueraria*, especially significant amounts of each of the herbs, and more particularly mixtures of each of the herbs approximately or precisely as set forth in one of Table 2, Table 3 or Table 4. Such mixtures of herbs may be made in a convention manner: that is by weighing out an appropriate amount of each herb and combining the various herbs to form the herbal mixture. This process may include additional steps, such as grinding or agitating the mixture. The mixture may be consumed as is, or it may be present in one or more capsules suitable for oral administration to a subject. In particular embodiments, the herbal mixture may be further processed, such as by preparing an extract of the mixture.

An extract of an herbal mixture according to the present invention may be prepared in a conventional manner, such as by combining the herbal mixture with one or more solvents for a time and under conditions suitable for preparing the extract. After the herbal mixture and solvent have been in contact for a period of time suitable to form the extract, the solvent and herbs are separated by a suitable method, such as filtering or centrifugation. The liquid comprising the solvent represents the extract. This extract can then be further processed, such as by reducing or dehydrating the extract, combining the extract with further ingredients, or both.

Suitable solvents for the extraction process (extraction solvents) include aqueous solvents, such as pure water and aqueous solutions of ethanol. Suitable conditions include applying heat to the mixture of extraction solvent and herbs. In certain embodiments, the solvent and herbal mixture are heated to boiling for a period of time. In particular embodiments, the herbal mixture is combined with water and the combination is boiled for a period exceeding about 1 minute, especially for a period exceeding 5 minutes.

In a particular embodiment of the invention, the herbal mixture set forth in Table 5, above, is combined with water and then heated to the boiling point for a period of time suitable to prepare an extract. After separating the water from the boiled herbs, water is removed by dehydration and the remaining residue is collected as a composition according to the invention (dehydrated extract). This dehydrated extract may then be diluted with hot water and drunk as a tea, or it may be combined with other flavorings or prepared in one or more gelatin capsules.

A method of the invention comprises consuming an amount of the invention compositions sufficient to treat a symptom of menopause. A "symptom of menopause" is a symptom associated with one or more of peri-menopause, menopause or post-menopause. Symptoms of menopause include hot flashes and sweating secondary to vasomotor instability, fatigue, irritability, insomnia, inability to concentrate, depression, memory loss, headache, anxiety, nervousness, intermittent dizziness, paresthesias, palpitations, tachycardia, nausea, constipation, diarrhea, arthralgia, myalgia, cold hands and feet, weight gain, urinary incontinence, vaginal dryness and loss of pelvic muscle tone. In particular embodiments, the method includes treatment of hot flashes.

The term treatment and its grammatical variants include reducing the frequency or severity of a particular symptom. The frequency of a symptom may be determined in an art-recognized manner, such as by one or more automated biometric methods (measurement of blood pressure, pulse rate, breathing rate, breathing volume, electrocardiogram, skin resistivity, electroencephalogram, etc.) or by requesting the subject to record the frequency of the symptom on a questionnaire. The severity of a symptom may also be determined by one or more of the aforementioned biometric methods or by questionnaire. Thus, measurement of frequency and severity of symptoms may be subjective, objective or both.

An amount of an invention composition sufficient to treat a symptom of menopause is thus an amount of the mixture of herbs, extract of the mixture of herbs, or mixture of extracts of herbs sufficient to reduce the frequency of the menopausal symptom, ameliorate the severity of the symptom, or both. In general, the amount needed to treat a symptom will depend upon the subject's age, weight, general health, genetic makeup, emotional condition, and other factors. The effective amount may be chosen to be more or less effective than estrogen hormone replacement therapy. Thus, an amount of an invention composition suitable for a daily dose will be equivalent to about 0.01 to 100 grams of an herbal mixture of the invention per kilogram body weight of the subject, and more particularly about 0.05 to about 50 grams per kilogram body weight of the subject. In terms of an extract according to the invention, the daily dose will be in the range of about 1 to 10,000 mg of dry extract per kg body weight, more particularly about 2 to about 5,000 mg/kg. The person skilled in the art will recognize that, although the invention compositions are believed to be safe, and in particular to present a reduced risk of causing estrogen replacement-related problems such as increased risk of breast cancer, nonetheless the lowest dose capable of reducing the menopausal symptom should be used. The person skilled in the art will likewise be able to titrate the dose necessary to achieve the desired symptom-relieving effect within the stipulated ranges, and will likewise recognize that upward or downward deviations from those ranges may be tolerated within the scope of the present invention.

Despite compelling evidence that estrogens cause breast cancer, observational studies paradoxically show that women in Asian countries have the lowest incidence of breast cancer even though they consume large quantities of plant estrogens (phytoestrogens). Likewise, Asian women report minimal symptoms during menopause and are far less prone to experience hot flashes at the time of cessation of ovarian function. These findings have encouraged many menopausal women in the United States to take phytoestrogens present in soybeans or herbal therapies as an alternative to estrogen, hoping to alleviate hot flashes without increasing their risk of developing breast cancer. Different estrogenic compounds may exert opposite effects on breast cells. Estrogens, such as estradiol ($E_2$), promote breast cancer, whereas phytoestrogens may contribute to the low incidence of breast cancer that is observed in Asia. Although there are substantial laboratory and observational data to support this theory (Kurtzer M. Phytoestrogen supplement use by women. J. Nutr. 2003; 133: 1983S-1986S), to date no randomized controlled studies have documented that phytoestrogens reduce breast cancer risk.

EXAMPLES

In order to demonstrate various aspects and advantages of the invention, the following illustrative examples have been presented. While the examples illustrate particular embodiments of the invention, the person skilled in the art will recognize that the full scope of the invention is not limited by these examples.

Preparative Example 1

MF11 (IND 58,267)

In a particular embodiment of the invention, the extract is designated MF101, which is shown in Table 5, below.

TABLE 5

Herbal Components in MF101 (IND 58,267)

| Pin Yin (Chinese Name) | Pharmacological Name | Daily Dose (grams)[1] | % In Starting Formula | Dry Weight[2] mg | % |
|---|---|---|---|---|---|
| Ban Zhi Lian | Herba Scutellaria Barbata | 30 | 10.7 | 906 | 7.2 |
| Shan Dou Gen | Radix Sophora Subprostratae | 30 | 10.7 | 708 | 5.6 |
| Zhi Mu | Radix Anamarrhena | 12 | 4.0 | 1459 | 11.6 |
| Hei Dou | Semen Glycine Sojae | 20 | 7.0 | 336 | 2.7 |
| Gan Cao | Radix Glycyrrhiza | 8 | 3.0 | 638 | 5.1 |
| Da Huang | Rhizoma Rhei | 8 | 3.0 | 586 | 4.7 |
| Fu Xiao Mai | Fructus Tritici Levis | 15 | 5.4 | 450 | 3.6 |
| Huang Qi | Radix Astragali | 12 | 4.0 | 612 | 4.9 |
| Sheng Di Huang | Radix Rehmania | 12 | 4.0 | 1865 | 14.9 |
| Nu Zhen Zi | Fructus Ligustri Lucidi | 15 | 5.4 | 762 | 6.1 |
| Suan Zao Ren | Semen Zyziphi Spinozae | 10 | 3.6 | 280 | 2.2 |
| Lian Zi Xin | Plumula Nelumbinis | 10 | 3.6 | 500 | 4.0 |
| Fu Ling | Poria Cocos | 10 | 3.6 | 38 | 0.3 |
| Ze Xie | Rhizoma Alismatis | 10 | 3.6 | 200 | 1.6 |
| Mu Dan Pi | Cortex Moutan Radicis | 8 | 3.0 | 258 | 2.1 |
| Shan Zhu Yu | Fructus Corni | 10 | 3.6 | 414 | 3.3 |
| Huai Niu Xi | Radix Achyranthis | 10 | 3.6 | 1260 | 10.0 |
| Mu Li | Concha Ostrea | 12 | 4.0 | 238 | 1.9 |
| Tian Men Dong | Radix Asparagi | 12 | 4.0 | 12 | 0.1 |
| Ge Gen | Radix Pueraria | 10 | 3.6 | 246 | 2.0 |
| Bai Zhu | Radix Atractylodis Macrocephala | 10 | 3.6 | 578 | 4.6 |
| Yin Yang Huo | Herba Epimedi | 8 | 3.0 | 192 | 1.5 |
| Total | | 282 | 100.0 | 12,538 | 100.0 |

[1]Daily dose refers to starting dose of herbs prior to boiling.
[2]Dry weight is determined on the single herb daily amount treated in the same manner, hence an approximation of dry weight in the resultant formula since all herbs are prepared together; the resultant dry weight of the entire formula boiled together is approximately 9,000 mg.

The dry extract is then diluted to a concentration of 53 mcg of solid extract per liter of extract solution. This solution is used throughout Examples 1-10, below.

Example 1

ERβ-Specific In Vitro ERE Activation of MF101

Figure 1B:
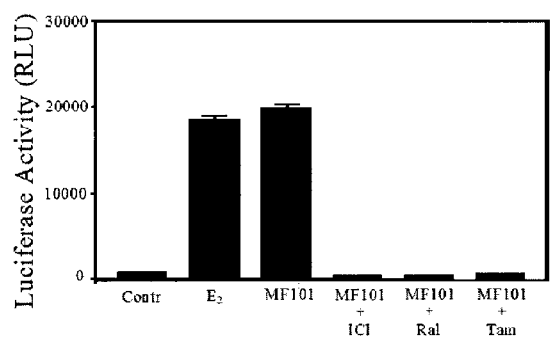
FIG. 1B is a bar graph comparing the effect of $E_2$, MF101 and combinations of MF101+ICI, MF101+raloxifene (Ral) and MF101+tamoxifen (Tam). The activation of ERE-tk-Luc by MF101 was blocked by ICI, Ral and Tam.
Figure 1C:
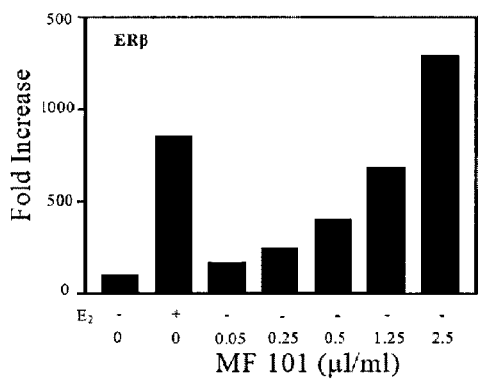
FIG. 1C is a bar graph showing the increase in keratin 19 mRNA expression in U2OS-ERβ cells in the presence of MF101.
Figure 1D:
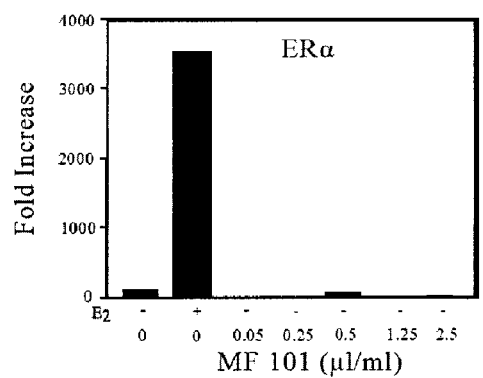
FIG. 1D is a bar graph showing that MF101 had almost no effect on keratin 19 mRNA expression in U2OS-ERα cells.

U2OS osteosarcoma cells were cotransfected with a classic ERE upstream of a minimal thymidine kinase (tk) promoter (ERE-tk-Luc) and expression vectors for human ERα or ERβ. MF101 produced a dose-dependent activation of ERE-tk-Luc with ERβ, but no activation was observed with ERα (FIG. 1A). ERβ produced a 2.5-fold activation of ERE-tk-Luc with 0.1 µl/ml MF101 and a maximal 20-fold activation occurred with 2.5 µl/ml MF101. The maximal activation by MF101 (2.5 µl/ml) was equivalent to that observed with 10 nM estradiol ($E_2$). The activation of ERE-tk-Luc by MF101 was blocked by ICI, raloxifene and tamoxifen (FIG. 1B) indicating that the effect of MF101 is mediated directly through ERβ. The ER-subtype selectivity was also examined on the endogenous keratin 19 gene, which contains an ERE. (Choi, I., Gudas, L. J. & Katzenellenbogen, B. S., "Regulation of keratin 19 gene expression by estrogen in human breast cancer cells and identification of the estrogen responsive gene region," Mol. Cell Endocrinol. 164, 225-37. (2000)). It had been previously shown that $E_2$ produced a dose-dependent stimulation of keratin 19 mRNA in U2OS cells stably transfected with a tetracycyline-inducible ERα or ERβ cells (Kian Tee, M. et al., "Estradiol and Selective Estrogen Receptor Modulators Differentially Regulate Target Genes with Estrogen Receptors {alpha} and {beta}," Mol. Biol. Cell 15, 1262-1272 (2004)). In contrast, MF101 increased keratin 19 mRNA in U2OS-ERβ cells (FIG. 1C), but not U2OS-ERα cells (FIG. 1D). These results demonstrate that MF101 selectively triggers ERβ-mediated transcriptional pathways at an ERE linked to a heterologous promoter or present in an endogenous gene.

Example 2

In Vitro Estrogen Receptor Binding

Figure 2A:
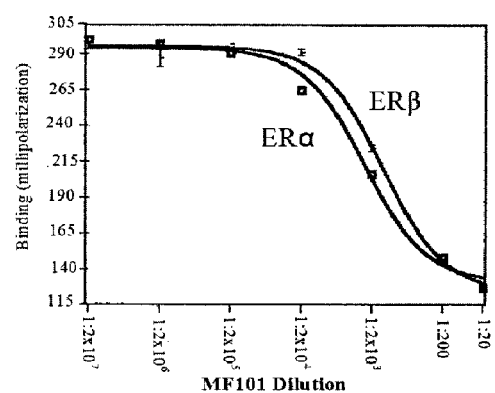
FIG. 2A is a line graph showing the binding of MF101 to ERβ and ERα.
Figure 2B:
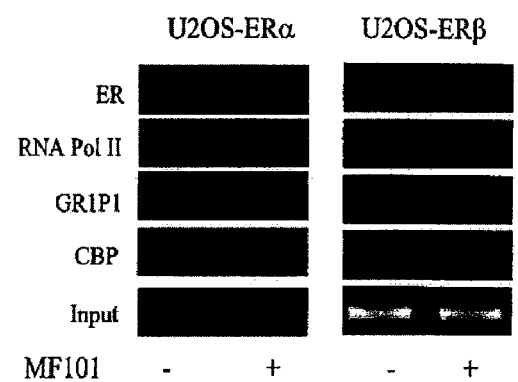
FIG. 2B is a gel demonstrating that MF101 recruits ERβ, but not ERα to the keratin 19 ERE.

Previously, it was shown that phytoestrogens found in soybeans, such as genistein bind to ERβ with a 7-30-fold higher affinity compared to ERα. (Barkhem, T. et al. Differential response of estrogen receptor alpha and estrogen receptor beta to partial estrogen agonists/antagonists. *Mol Pharmacol.* 54, 105-12 (1998); Kuiper, G. G. et al. Interaction of estrogenic chemicals and phytoestrogens with estrogen receptor beta. *Endocrinology* 139, 4252-63 (1998)). The data in FIGS. 1A-1D suggest that MF101 may act in an ERβ-selective manner by binding better to ERβ. The ability of MF101 to compete with $E_2$ binding to purified ERα and ERβ was studied in in vitro binding assays. Competition binding curves show that MF101 binds equally to ERβ and ERα (FIG. 2A). These experiments suggest that the ERβ-selectivity of MF101 is not due to preferential binding to ERβ. Another possibility is that the ERβ-selectivity of MF101 results from selective binding of MF101-ERβ complex to EREs in target genes. To investigate this possibility, chromatin immunoprecipitation (ChIP) assays were performed with the keratin 19 gene in U2OS-ERβ and U2OS-ERα cells. Previously, it was reported that $E_2$ treatment leads to the recruitment of ERα and ERβ in the U2OS-ERα and U2OS-ERβ cells, respectively. (Kian Tee, M. et al., "Estradiol and Selective Estrogen Receptor Modulators Differentially Regulate Target Genes with Estrogen Receptors {alpha} and {beta}," *Mol. Biol. Cell* 15, 1262-1272 (2004)). In contrast, ChIP shows that MF101 recruited ERβ, but not ERα to the keratin 19 ERE (FIG. 2B). Thus, binding of MF101 to ERα does not produce a conformation that allows it to bind an ERE.

Example 3

Elastase Inhibition by MF101

Figure 2C:
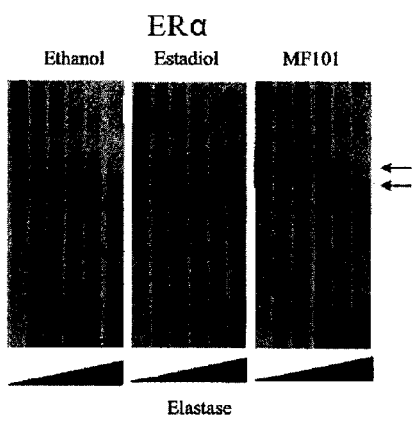
FIG. 2C is a gel demonstrating the effect of ethanol (control), $E_2$ (positive control) and MF101 on elastase digestion of ERα. When bound with MF101, ERα demonstrates a slight increase in protection to elastase compared to the control.
Figure 2D:
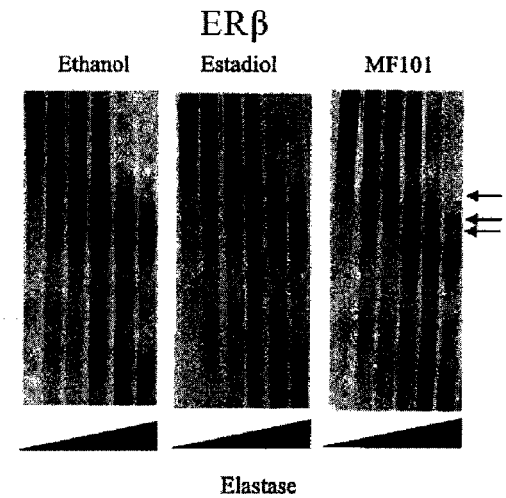
FIG. 2D is a gel demonstrating the effect of ethanol (control), $E_2$ (positive control) and MF101 on elastase digestion of ERβ.

To further investigate the effects of MF101 on the conformation of ERα and ERβ, limited proteolysis with elastase was performed to determine if MF101 causes a different protease digestion pattern compared to $E_2$. After digestion with elastase, ERα gives a distinct pattern of protection with $E_2$ and MF101 (FIG. 2C). The strongest protection of ERα is observed when ERα is bound with $E_2$. The two arrows indicate several protected fragments are present even at the highest elastase concentrations. In the absence of ligand (ethanol control), there is an obvious loss of protection of ERα. When bound with MF101, ERα demonstrates a slight increase in protection to elastase compared to the control, but not as much protection occurred compared to ERα bound to $E_2$ (FIG. 2D). In contrast, the protease protection results with ERβ, produces a completely different pattern of protected fragments compared to ERα. MF101 produced a distinct pattern compared to ethanol and $E_2$. (Compare the 5 arrows indicating protected fragments in the $E_2$ and ethanol control and the 4 arrows indicating protected fragments in the MF101 sample). This suggests that upon binding MF101, ERβ adopts a different overall conformation than when bound with $E_2$ or no hormone. Because the ERβ has different conformation when bound with MF101, different surfaces of ERβ are exposed and potentially available for coregulatory proteins. Whether MF101 causes a differential recruitment of coregulatory proteins to ERα and ERβ was examined, because conformational changes in ER are known to lead to the recruitment of distinct classes of proteins, including p160 coactivators. (Shang, Y., Hu, X., DiRenzo, J., Lazar, M. A. & Brown, M. Cofactor dynamics and sufficiency in estrogen receptor-regulated transcription. *Cell* 103, 843-52. (2000); Metivier, R. et al. Estrogen receptor-alpha directs ordered, cyclical, and combinatorial recruitment of cofactors on a natural target promoter. *Cell* 115, 751-63 (2003); Smith, C. L. & O'Malley, B. W., "Coregulator function: a key to understanding tissue specificity of selective receptor modulators," *Endocr. Rev.* 25, 45-71 (2004)).

To determine whether MF101 selectively recruits coregulators to an endogenous gene, ChIP assays were performed on the keratin 19 gene in U2OS-ERα and U2OS-ERβ cells. MF101 induced recruitment of GRIP1 and CBP to the keratin 19 gene in U2OS-ERβ cells, but not in the U2OS-ERα cells (FIG. 2B). MF101 also selectively recruited RNA polymerase II to ERβ, which is consistent with the finding that MF101 only activated the keratin 19 gene in U2OS-ERβ cells. These results demonstrate that the ERβ-selectivity of MF101 results from differential binding to EREs and recruitment of coregulatory proteins to target genes.

Example 4

MF101 Does Not Stimulate In Vitro MCF-7 Breast Cancer Cell Proliferation

Figure 3A:
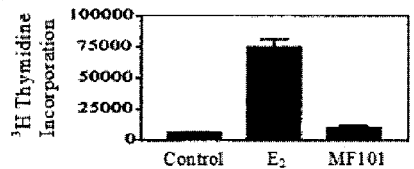
FIG. 3A is a bar graph showing the difference in $^3$H-Thymidine incorporation in cells treated with control, $E_2$ and MF101, respectively. In general, MF101 did not increase $^3$H-Thymidine incorporation greatly over the control.

A critical feature of an alternative estrogen for hot flashes is that it not promote breast cancer. The growth-promoting properties of MF101 were studied in MCF-7 breast cancer cells, which express only ERα (FIG. 3A). MCF-7 cells were treated with MF101 for 7 days and cell proliferation was measured by $^3$H-thymidine incorporation. Unlike $E_2$, MF101 did not stimulate cell proliferation of MCF-7 cells. MF101 also did not activate the c-myc and cyclin D1 genes (FIG. 3B), which are key genes activated by $E_2$ to promote cell proliferation and breast cancer. These data provide further evidence that MF101 is ERβ-selective, and are consistent with the foregoing studies demonstrating that ERα mediates the proliferative effects of $E_2$ in MCF-7 cells. (Paruthiyil, S. et al., "Estrogen receptor beta inhibits human breast cancer cell proliferation and tumor formation by causing a G2 cell cycle arrest," *Cancer Res.* 64, 423-8 (2004); An, J., Tzagarakis-Foster, C., Scharschmidt, T. C., Lomri, N. & Leitman, D. C., "Estrogen receptor beta-selective transcriptional activity and recruitment of coregulators by phytoestrogens," *J. Biol. Chem.* 276, 17808-14. (2001)).

Figure 3D:
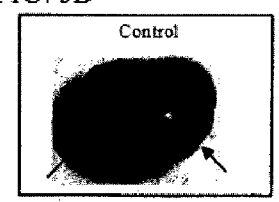
FIGS. 3D-F are photographs showing the effect of controls, diethylstilbestrol (DES) and MF101 on cell growth.
Figure 3G:
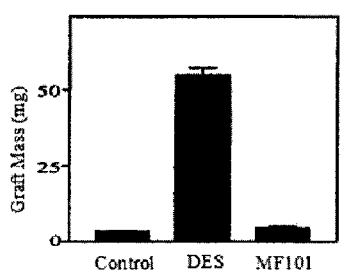
FIG. 3G is a bar graph showing the effect of control, DES and MF101 on the growth of a xenograft. MF101 did not stimulate graft growth, while DES provoked a substantial increase in xenograft mass.
Figure 3B:
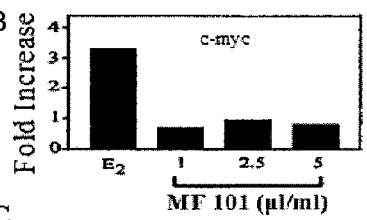
FIGS. 3B and 3C are bar graphs showing that MF101 also did not activate the c-myc (FIG. 3*b*) and cyclin D1 (FIG. 3*c*) genes in cells.
Figure 3E:
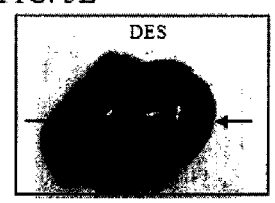
Figure 3C:
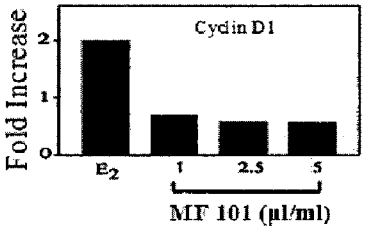
Figure 3F:
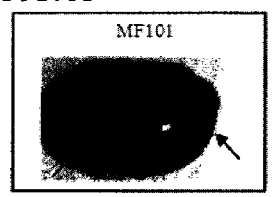
Figure 3H:
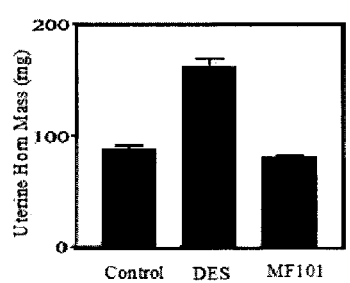
FIG. 3H is a bar graph showing the effect of control, DES and MF101 on the growth of a uterine horn mass. MF101 did not stimulate uterine horn growth, in contrast with DES, which stimulated a substantial increase in uterine horn growth.

In a similar experiment, the effect of MF101 on breast cancer cells was compared to that of diethylstilbestrol (DES). FIGS. 3D-3F show the proliferation-stimulating effect of DES on the breast cancer, as compared to the control-treated (FIG. 3D) and the MF101-treated (FIG. 3F) cancer cells. FIGS. 3G and 3H show the effect of control, DES and MF101 on a breast cancer graft mass (FIG. 3G) and a uterine horn mass (FIG. 3H). These results demonstrate that unlike the synthetic estrogen DES, MF101 does not stimulate proliferation of either cancer cells or normal uterine cells.

Example 5

Gene Expression Microarrays

Based on the studies outlined below, the inventors have hypothesized that estrogens promote breast cancer by interacting with ERα, whereas the phytoestrogens found in MF101 may prevent breast cancer and menopausal symptoms such as hot flashes by selectively interacting with ERβ, which represses growth-promoting genes and inhibits ERα-mediated proliferation of breast cells. ERβ receptor is more prevalent in non-reproductive tissues such as the brain and bone which may play a role in how phytoestrogens could decrease central nervous system effects that cause vasomotor symptoms and help to maintain bone mass.

Estrogenic compounds elicit their clinical effects by interacting with two distinct estrogen receptors, which are members of the steroid receptor superfamily. (Evans R M. The steroid and thyroid hormone receptor superfamily, Science 1988;240: 889-895; Mangelsdorf D J, Thummel C, Beato M, et al., The nuclear receptor superfamily: the second decade. Cell; 83: 835-839.) ERα is a 595-amino acid protein, and a second ERα (530 amino acids) termed ERβ was identified a decade later. (Mosselman S, Polman J, Dijkema R. ER beta: identification and characterization of a novel human estrogen receptor. FEBS Lett. 1996;392:49-53.) The functional differences between these two receptors have only recently been explored. The overall structures of the ERα and ERβ are very similar except for the A/B domain, which exhibits only a 25% homology and contains one of the transactivating regions. The DNA binding domain is virtually identical (98% homology), whereas only 55% of the amino acids are conserved in the ligand-binding domain, which also contains the second transactivating domain. (Enmark E, Pelto-Huikko M, Grandien K, et al. Human estrogen receptor beta-gene structure, chromosomal localization, and expression pattern. J Clin. Endocrinol. Metab. 1997;82:4258-4265.) Other studies clearly show that the tissue distribution, physiological effects and transcriptional activities are quite different. ERβ is more ubiquitous, and is expressed in many non-reproductive tissues, such as bone, brain, urinary tract, vascular system and prostate gland, in addition to reproductive tissues, such as the ovary and testis. ERα is expressed mainly in the uterus, liver, breast and kidney. The different physiological roles of ERα and ERβ have been definitely demonstrated in ERα or ERβ knockout mice. The ERα knockout mice develop major defects, such as primitive mammary glands and uterus, and are infertile. (Hewitt S C, Korach K S., "Oestrogen receptor knockout mice: roles for oestrogen receptors alpha and beta in reproductive tissues," Reproduction 2003;125:143-149.) In contrast, the effects observed in the ERβ knockout mice have been more subtle, including subfertility, with decreased litter size, thickening of female cortical bone and prostate hyperplasia.

Phytoestrogens have been long known to exert estrogenic effects through binding of steroid hormone receptors (Tamaya T, Sato S, Okada H H, "Possible mechanism of steroid action of the plant herb extracts glycyrrhizin, glycyrrhetinic acid, and paeoniflorin: inhibition by plant herb extracts of steroid protein binding in the rabbit," Am. J. Obstet. Gynecol., 1986, 155:1134-1139) and more recently have been found to possess a significantly higher affinity for ERβ compared to ERα. (Barkhem T, Carlsson B, Nilsson Y, et al., "Differential response of estrogen receptor alpha and estrogen receptor beta to partial estrogen agonists/antagonists," Mol. Pharmacol., 1998, 54:105-112.) In initial experiments, it was shown that the isoflavone genistein is a potent transcriptional agonist for ERβ, but only weakly so for ERα. (An J, Tzagarakis-Foster C, Scharschmidt T C, et al., "Estrogen receptor beta-selective transcriptional activity and recruitment of coregulators by phytoestrogens," J. Biol. Chem. 2001, 276:17808-17814.) In order to identify ER-subtype selective natural compounds for menopausal symptoms it was necessary to demonstrate that ERα or ERβ exert distinct biological effects. ERα and ERβ regulate different target genes, as is demonstrated using human U2OS osteosarcoma cells that are stably transfected with a tetracycline-inducible vector to express ERα or ERβ. Western blotting, immunohistochemistry and immunoprecipitation studies confirmed that U2OS-ERα cells synthesized only ERα, and that U2OS-ERβ cells expressed exclusively ERβ. (Kian Tee M, Rogatsky I, Tzagarakis-Foster C, et al., "Estradiol and selective estrogen receptor modulators differentially regulate target genes with estrogen receptors alpha and beta." Mol. Biol. Cell 2004, 15:1262-12672.) After an 18 h treatment with doxycycline to induce the expression of ERα or ERβ, the U2OS-ERα and U2OS-ERβ cell lines contained 69,000 and 54,000 receptors per cell by $^3$H-$E_2$ binding studies, respectively. To identify genes regulated by ERα and/or ERβ, the U2OS-ERα and U2OS-ERβ cell lines were treated with doxycycline for 18 h in the absence or presence of 10 nM $E_2$. Total RNA was used to prepare cRNA for hybridization with the human U95Av2 Affymetrix microarrays, which contain 12,600 known genes. Six sets of comparative expression data of untreated vs. each treated group were used to determine the genes regulated in ERα or ERβ cells. In both U2OS-ERα and U2OS-ERβ cells, a total of 228 were significantly ($p<0.05$) activated or repressed by $E_2$ (Table 4). $E_2$ regulated 65 genes only in the U2OS-ERα cells, and 125 genes only in the U2OS-ERβ cells. $E_2$ repressed 32 genes in U2OS-ERα cells, and 38 genes in U2OS-ERβ cells. Only 34 genes were activated and 4 genes repressed by $E_2$ in both cell lines. These findings demonstrate that only 38 of the 228 (17%) genes are regulated by both ERα and ERβ with $E_2$. Similar to $E_2$, the genes regulated by raloxifene or tamoxifen in the U2OS-ERα cells were distinct from those regulated in the U2OS-ERβ cells. Surprisingly, only 27% of the genes regulated by tamoxifen were also regulated by raloxifene even though they are both classified as selective estrogen receptor modulators (SERMs). These results are summarized in Table 6, below.

TABLE 6

Differential Gene Regulation via ERα and ERβ Using Various ER Ligands

| | Activated | Repressed | Selected genes | Mean signal log ratio ± S.E. | Fold-change by real-time PCR |
|---|---|---|---|---|---|
| Estradiol: 228 genes regulated in U2OSα and U2OSβ cell lines | | | | | |
| α | 33 (14.5%) | 32 (14%) | α-antitrypsin | 1.63 ± 0.18 (α) | 1.76 (α) |
| α + β | 34 (14.9%) | 4 (1.8%) | Keratin 19 | 5.45 ± 0.97 (α); 3.55 ± 0.38 (β) | 38.21 (α); 317.37 (β) |
| | | | WISP-2 | 2.43 ± 0.39 (α); 0.83 ± 0.15 (β) | 4.46 (α); 2.27 (β) |
| β | 87 (38.2%) | 38 (16.7%) | Mda-7 | 4.68 ± 0.78 (β) | 54.76 (β) |

TABLE 6-continued

Differential Gene Regulation via ERα and ERβ Using Various ER Ligands

| | Activated | Repressed | | Selected genes | Mean signal log ratio ± S.E. | Fold-change by real-time PCR |
|---|---|---|---|---|---|---|
| | | Raloxifene: 190 genes regulated in U2OSα and U2OSβ cell lines | | | | |
| α | 10 (5.3%) | | 10 (5.3%) | | | |
| α + β | | 17* (8.9%) | | NKG2C | 2.40 ± 0.82 (α); −5.20 ± 0.08 (β) | 7.54 (α); 0.36 (β) |
| β | 52 (27.4%) | | 101 (53.2%) | | | |
| | | Tamoxifen: 236 genes regulated in U2OSα and U2OSβ cell lines | | | | |
| α | 21 (8.9%) | | 38 (16.1%) | | | |
| α + β | 1 (0.4%) | 12* (5.1%) | 9 (3.8%) | NKG2E | 2.23 ± 0.62 (α); −5.20 ± 0.73 (β) | 4.64 (α); 0.62 (β) |
| β | 26 (11%) | | 129 (54.7%) | | | |

Differential Gene Regulation by $E_2$ and SERMs in the U2OS-ERα and U2OS-ERβ cell lines.

Doxycycline-induced U2OS-ERα and U2OS-ERβ cells were treated with 10 nM $E_2$, 1 μM raloxifene or 1 μM tamoxifen for 18 h. Microarray data obtained from human Affymetrix U95Av2 gene chips from untreated vs. ligand-treated samples were analyzed using the Affymetrix Microarray Suite Version 5.0. Candidate genes displaying a statistically significant (p<0.05) increase or decrease signal changes relative to controls in at least three experiments were further selected by a ±0.8 signal log ratio mean cut-off. The numbers of genes activated, repressed and their relative percentages (in parentheses) in ERα, ERβ and both ERα+ERβ cell lines are shown. Asterisks (*) indicate the number of common genes regulated by SERMs in the ERα cells that displayed opposite expression patterns compared to ERβ cells. Real-time RT-PCR on α-antitrypsin, keratin 19 (K19), WISP-2, Mda-7, NKG2C and NKG2E was performed on U2OS-ERα and U2OS-ERβ samples treated for 18 h with either 10 nM $E_2$, 1 μM raloxifene or 1 μM tamoxifen. Fold-changes in the U2OS-ERα and U2OS-ERβ samples (in parentheses) were calculated relative to the untreated samples.

The observation that ERα and ERβ regulate distinct genes, suggests that ERα and ERβ may have different roles in breast cancer development. To investigate the role of ERα in breast cancer, the effects of $E_2$ on cell proliferation in MCF-7 cells that express only ERα were studied. $E_2$ produced a dose-dependent increase in cell number in ERα-MCF-7 cells. (An, supra, 2001). This study demonstrated that the proliferative effects are mediated by ERα, because these cells do not express ERβ. To investigate the role of ERβ on the proliferation of breast cancer cells, an adenovirus (Ad) was used to deliver ERβ into a high percentage of cells. MCF-7 cells were infected for 24 h with Ad-ERβ or Ad-LacZ to control for potential non-specific effects of the virus. The infected cells were grown for 10 days in the absence or presence of $E_2$, after which DNA synthesis was measured by [$^3$H] thymidine incorporation in vitro. The expression of ERβ resulted in a 50% reduction in cell proliferation of MCF-7 cells in the absence of $E_2$ compared to cells infected with 50 MOI of Ad-LacZ (FIG. 4). $E_2$ augmented the inhibition of cell proliferation to 70% in the Ad-ERβ-infected cells. Similar results were observed using 100 multiplicity of infection (MOI) of Ad-ERβ. The observation that the inhibition of cell proliferation by ERβ was predominantly ligand-independent may result from residual $E_2$ in stripped serum or retained in cells infected with ERβ, or unliganded properties of ERβ.

The effects of expressing ERβ on tumor formation in a mouse xenograft model were also explored (FIG. 5). MCF-7 cells infected with adenoviruses that express LacZ, ERα or ERβ were initially aggregated, then resuspended in polymerized collagen gel and grafted under the kidney capsule of female nude mice implanted with a subcutaneous estradiol pellet. One-month after the cells were grafted, tumors of comparable size developed from non-infected MCF-7 cells and cells infected with Ad-LacZ or Ad-ERβ. No significant tumor developed from MCF-7 cells infected with Ad-ERβ (lower right). The Ki67 proliferation index found that approximately 70% of non-infected MCF-7 cells and cells infected with Ad-LacZ or Ad-ERα stained for Ki67 compared to 5% of cells infected with Ad-ERβ (data not shown).

These studies demonstrate that introducing Ad-ERβ into MCF-7 cells, but not Ad-ERα prevents tumor formation in mouse xenografts. Similar levels of expression of ERα and ERβ were detected in the infected cells by immunoblots (data not shown) making it unlikely that these results are due to over-expression and non-specific squelching of cofactors or transcription factors by ERβ. Furthermore, if squelching was the mechanism whereby ERβ prevents tumor formation then similar results should have been observed with cells infected with Ad-ERα.

Example 6

MF101 Does Not Functionally Interact With Estrogen Receptor Alpha (ERα)

To determine if MF101 is an agonist for ERα, which could exert unwanted proliferative effects on breast and uterine cells, thereby potentially increasing breast and uterine cancer risk, ERα was transiently transfected into ER-negative U2OS osteosarcoma cells. An estrogen response element-thymidine kinase (tk)-luciferase (ERE-tk-Luc) construct was transiently co-transfected into the cells. MF101 or estradiol was then added at physiological concentrations and the cells were incubated for 18 hours at which time luciferase activity was measured. As seen in FIG. 6, MF101 does not activate ERα; however, estradiol activates ERα, and this transactivating activity can be inhibited by the pure estrogen antagonist, ICI 182,780 (ICI).

Example 7

MF101 Causes Estrogen Receptor Beta (ERβ) Selective Transcriptional Activation

To study the ERβ-mediated effects of MF101, ERβ was transiently transfected into U2OS osteosarcoma cells. The ERE-tk-Luc construct was transiently co-transfected. MF101 or estradiol were then added at physiological concentrations for 18 hours, and luciferase activity was measured. As shown in FIG. 7, MF101 activates ERβ. Both MF101 and estradiol activate ERβ, and this activity is blocked by ICI 182,780. The results suggest that estradiol universally interacts with both ERα and ERβ, while MF101 selectively interacts with ERβ only.

Example 8

MF101 Exhibits Antiproliferative Activity on Breast Cancer Cells

The objective in the next set of laboratory studies was to exclude a proliferative effect of MF101 on breast cancer cells in vitro. FIG. 8 demonstrates that MF101 exhibits anti-proliferative activity on ER-positive breast cancer cells using the Cy-Quant Molecular Devise system. MCF7 cells express endogenous ERα, while SKBR3 cells are ER-negative. MF101 shows greater inhibition on the ER positive cells. This suggests an ER-independent anti-proliferative effect and no evidence of growth stimulation.

Example 9

MF101 Protects Bone Cells from the Activity of TNF beta and May Prevent Osteoporosis In bone, estrogen is felt to repress certain estrogen suppressible genes like tumor necrosis factor β (TNFβ) and thereby mediate its bone mineralization protection effect. To observe the potential effect of MF101 on bone cells, ERβ (the more abundant ER in the bone) was transiently transfected into U2OS osteosarcoma cells. TNFβ-tk-response element-luciferase construct (TNF-RE-tk-Luc) was transiently co-transfected into the cells, MF101 or estradiol was added and luciferase activity was measured after 18 hours. Both MF101 and estradiol inhibited tumor TNFβ, which inhibition was blocked by ICI 182,780 (ICI). The data shown in FIG. 9 suggest both estradiol and MF101 would be effective at maintaining bone mass in postmenopausal women.

Example 10

ER Selectivity of Individual Herbal Components of MF101

The ERα and ERβ transcriptional activities of several of several individual herbs have also been assessed. Since one object of the invention is to test the entire MF101 formula, in keeping with the traditional Chinese medical approach, laboratory tests have been focused on the entire formula. However, of 67 herbs screened in a transient transfection assay, 33 exhibited activity with ERE-tk-Luc or TNF-RE-tk-Luc reporters, and 8 demonstrated ERα selectivity, while 4 had ERβ selectivity.

Example 11

Feasibility and Toxicity Data from the Completed Phase I Clinical Trial of MF101

A Phase I trial was conducted at the University of San Francisco, Calif., to assess the safety and feasibility of MF101 to alleviate hot flashes and other symptoms associated with menopause. The study was an uncontrolled, open-label trial among 31 healthy post-menopausal women aged 50 to 65 who reported at least 56 hot flashes during a 7-day period. Participants were treated with 5 grams of granulated MF101 as a powder mixed with warm water, taken orally, twice a day for 30 days. The primary outcome measure was safety and secondary outcomes included change in the frequency of hot flashes as well as effects on serum estradiol, vaginal maturity and bone resorption markers. The study included a 30-day run-in period followed by a 30-day treatment period with the study drug. Table 7 summarizes the number of study participants included in the analysis, those excluded and the reasons for exclusion.

TABLE 7

Summary of the Study Participants Included in the Analysis

| Subject Category | # Subjects |
| --- | --- |
| Study Participants Consented | 31 |
| Consented but not treated with MF101 | 2 |
| Included in Safety Analysis | 25 |
| Completed Study | 22 |
| Discontinued Treatment: | 7 |
| Loss to Follow Up | 4 |
| Adverse Effects | 2 |
| Unpleasant Taste | 1 |

On average, the study participants who completed the trial took 87.8% of the prescribed dose of MF101 over the 30-day treatment period. There were no reported Grade III or IV adverse events measured by NCI common toxicity criteria for the 25 participants with available toxicity data. There were a total of 9 adverse events reported by the study participants to the investigative physician and categorized as possibly or probably related to MF101. Five of the adverse events were categorized as Grade I, and four were recorded as Grade II adverse events according to the NCI common toxicity criteria. The most common toxicities reported were slight nausea or stomach bloating (4/25 women). The other five adverse events were for the following reasons: headache, lethargy, depression, mood changes and elevated blood pressure. None of the study participants required treatment for any reported side effects nor were there any hospitalizations.

All 22 participants who had baseline and study termination blood and urine laboratory tests were included in the analysis for toxicity. There were no statistically significant changes in any of the laboratory values for the complete blood count, chemistry, liver panel, or in serum or urinary estrogen or gonadotropin levels.

Although this study was not designed to measure efficacy as a primary endpoint, there was a statistically significant reduction in the frequency and severity of hot flashes after 30 days of treatment. The mean frequency of hot flashes was 57.3 per 7 days at baseline and 44.9 after treatment (p=0.003). The hot flash score (frequency multiplied by severity) decreased from 98.0 at baseline to 81.7 after treatment (p=0.03). Of the 22 women who completed the study, 18 (82%) had fewer hot flashes after 30 days of study medication while only 4 (18%) had more. There was a 22% reduction in the frequency of hot flashes experienced over a 7-day period measured at baseline as compared to the last 7 days on the study medication (p=0.0035). There was also a 17% reduction in hot flash score (frequency multiplied by severity) after 30 days of treatment (p=0.03 1).

In summary, preliminary clinical trial data indicate MF101 is safe for the treatment of hot flashes and can be feasibly administered with good compliance. MF101 reduced the frequency and severity of hot flashes; however, the effect was small. The results of this study are shown in Table 1, where it is shown that 7 of 22 patients demonstrated a greater than 40% reduction in the symptoms of menopause.

TABLE 1

| Percent Reduction | Number of Patients | Percent Total Patients who Completed the Study |
| --- | --- | --- |
| 0-10 | 8/22 | 36 |
| 11-20 | 4/22 | 18 |
| 21-30 | 3/22 | 14 |
| >40 | 7/22 | 32 |

Example 12

Increased Dose Study

A double-blind, placebo-controlled, randomized clinical trial for the Phase II study that is longer in duration than that set forth in Example 11, and that includes a comparison higher dose of MF101, is conducted. The dose of MF101 is 5 grams of dry weight of MF101 twice per day and 10 grams of dry weight of MF101 twice per day. The study medication is packaged in capsule form in an effort to reduce the number of gastrointestinal complaints that may arise from the bitterness of the herbal tea and to minimize withdraw from the study due to the unappealing taste of the liquid extract.

CONCLUSION

Based on the observations that ERα promotes breast cancer cell proliferation, whereas ERβ inhibits proliferation and tumor formation, ERβ-selective estrogens should not promote breast cancer and may prevent hot flashes. The results herein demonstrate that MF101 regulates gene transcription through ERβ by selectively recruiting coregulatory proteins. Unlike estrogens in hormone therapy, MF101 does not stimulate proliferation of MCF-7 cells, nor does it activate the proliferative genes, c-myc and cyclin D1, suggesting that MF101 does not promote breast cancer. In the study outlined in Example 11, above, MF101 did not elicit any adverse effects and produced a greater than 40% reduction in hot flashes in seven out of twenty-two women who completed the trial. These results demonstrate that MF101 contains ERβ-selective estrogens, which is consistent with MF101 being a safer alternative to non-selective estrogens used in hormone therapy to prevent hot flashes.

Many women are eagerly awaiting safe and effective alternatives to estrogens used in HT for menopausal symptoms after the results of the Women's Health Initiative trial, which showed that the risks of HT exceed the benefits. In the meantime a recent survey reported that 79% of peri- and postmenopausal women are using botanical dietary supplements (BDS). Despite the widespread use of BDS the mechanism of action, efficacy and safety of botanicals has not been rigorously examined. MF101 is a formula that contains 22 individual herbs used historically in Traditional Chinese Medicine (TCM) to alleviate hot flashes and other climacteric symptoms. The results herein demonstrate that MF101 has selective estrogen receptor activity that could be exploited clinically to prevent hot flashes.

The finding that MF101 is ERβ-selective provides a unique opportunity to investigate the role of ERβ in the treatment of hot flashes in women. As discussed above, a prospective, single-arm, phase 1 clinical trial was performed with MF101 in surgically-induced or naturally occurring healthy postmenopausal women between the ages of 40-60 who reported ≧7 moderate to severe hot flashes per day or ≧50 moderate to sever hot flashes per week. During the first 30-days of the trial (run-in period), baseline outcome measures were obtained, including a daily diary recording hot flash frequency and severity, as well as laboratory measures of hematologic values, blood chemistry, hepatic function, renal function and hormonal status. Following the run-in period, women were treated twice daily for 30 days with an oral, 5 µm MF101 extract that was reconstituted in water. At the end of the treatment phase the same outcome measures were repeated. Twenty-two women completed the trial. There was a statistically significant reduction in both the frequency and severity of hot flashes. The mean frequency of hot flashes dropped from 57.3 at baseline to 44.9 hot flashes per week after treatment (p=0.003, paired t-test) (data not shown). The hot flash score (frequency multiplied by severity) also decreased from 98.0 at baseline to 81.7 after treatment (p=0.031, paired t-test). Seven women reported a greater then 40% reduction in hot flashes (Table 1). These data suggest that MF101 decreases the frequency and severity of hot flashes in some women with moderate to severe symptoms.

The foregoing examples demonstrate that MF101 triggers only ERβ-mediated transcriptional pathways. Surprisingly, MF101 binds equally to purified ERα and ERβ. This observation indicates that screening compounds only for ligand binding activity with purified ERs may not be an effective strategy for drug discovery of ER-subtype specific compounds. It was determined that the ERβ-selectivity of MF101 results from its capacity to create a conformation that allows ERβ to bind to an ERE and recruit coregulators, such as GRIP1 and CBP. The selective recruitment of coactivators to ERβ by MF101 is clinically important because ERα mediates cell proliferation and tumor formation of MCF-7 breast cancer cells, whereas ERβ acts as a tumor suppressor in ER positive breast cancer cells. (Paruthiyil, S. et al., "Estrogen receptor beta inhibits human breast cancer cell proliferation and tumor formation by causing a G2 cell cycle arrest," *Cancer Res.* 64, 423-8 (2004); Strom, A. et al., "Estrogen receptor beta inhibits 17beta-estradiol-stimulated proliferation of the breast cancer cell line T47D," *Proc. Natl. Acad. Sci. USA* 101, 1566-71 (2004)). The lack of recruitment of coactivators to ERα could account for the observation that MF101 did not activate transcription of c-myc and cyclin D1 or stimulate proliferation of MCF-7 cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating hot flashes associated with, comprising administering to a menopausal subject an effective amount of an herbal composition to treat hot flashes associated with menopause, said herbal composition comprising an extract of a mixture of: Herba *Scutellaria barbata*, Radix *Sophora subprostrata*, Radix *Anemarrhena*, Semen *Glycine soja*, Radix *Glycyrrhiza*, Rhizoma *Rhei*, Fructus *Tritici levis*, Radix *Astragali*, Radix *Rehmannia*, Fructus *Ligustri lucidi*, Semen *Zyzipizi spinosae*, Plumula *Nelumbinis*, *Poria cocos*, Rhizoma *Alismatis*, Cortex *Moutan radicis*, Fructus *Corni*, Radix *Achyranthis*, Concha *Ostrea*, Radix *Asparagi*, Radix *Pueraria*, Radix *Atractylodis macrocephala* and Herba *Epimedium*.

2. The method of claim 1, wherein the amount of herbal composition administered to the subject is about 0.1-10 mg of herbal composition per kg body weight of the subject.

3. The method of claim 1, wherein the herbal composition is an extract of a mixture of herbs in proportions set forth in the following table:

| Herbal Ingredient | Proportion (percent by weight of total composition) |
| --- | --- |
| Herba Scutellaria barbata | 5-16% |
| Radix Sophora subprostrata | 5-16% |
| Radix Anamarrhena | 2-6% |
| Semen Glycine soja | 3.5-10.5% |
| Radix Glycyrrhiza | 1.5-4.5% |
| Rhizoma Rhei | 1.5-4.5% |
| Fructus Tritici levis | 2.5-7.5% |
| Radix Astragali | 2-6% |
| Radix Rehmannia | 2-6% |
| Fructus Ligustri lucidi | 2.5-7.5% |
| Semen Zyziphi spinosae | 1.8-5.4% |
| Plumula Nelumbinis | 1.8-5.4% |
| Poria Cocos | 1.8-5.4% |
| Rhizoma Alismatis | 1.8-5.4% |
| Cortex Moutan radicis | 1.5-4.5% |
| Fructus Corni | 1.8-5.4% |
| Radix Achyranthis | 1.8-5.4% |
| Concha Ostrea | 2-6% |
| Radix Asparagi | 2-6% |
| Radix Pueraria | 1.8-5.4% |
| Radix Atractylodis macrocephala | 1.8-5.4% |
| Herba Epimedium | 1.5-4.5%. |

4. The method of claim 1, wherein the herbal composition is an extract of a mixture of herbs in proportions set forth in the following table:

| Herbal Ingredient | Proportion (percent by weight of total composition) |
| --- | --- |
| Herba Scutellaria barbata | 7.5-12.5% |
| Radix Sophora subprostrata | 7.5-12.5% |
| Radix Anamarrhena | 3-5% |
| Semen Glycine soja | 5-9% |
| Radix Glycyrrhiza | 2-4% |
| Rhizoma Rhei | 2-4% |
| Fructus Tritici levis | 4-7% |
| Radix Astragali | 3-5% |
| Radix Rehmannia | 3-5% |
| Fructus Ligustri lucidi | 4-7% |
| Semen Zyziphi spinosae | 2.7-4.5% |
| Plumula Nelumbinis | 2.7-4.5% |
| Poria Cocos | 2.7-4.5% |
| Rhizoma Alismatis | 2.7-4.5% |
| Cortex Moutan radicis | 2-4% |
| Fructus Corni | 2.7-4.5% |
| Radix Achyranthis | 2.7-4.5% |
| Concha Ostrea | 3-5% |
| Radix Asparagi | 3-5% |
| Radix Pueraria | 2.7-4.5% |
| Radix Atractylodis macrocephala | 2.7-4.5% |
| Herba Epimedium | 2-4%. |

5. The method of claim 1, wherein the herbal composition is an extract of a mixture of herbs in proportions set forth in the following table:

| Herbal Ingredient | Approximate Proportion (percent by weight of total composition) |
| --- | --- |
| Herba Scutellaria barbata | 10.7% |
| Radix Sophora subprostrata | 10.7% |
| Radix Anamarrhena | 4.0% |
| Semen Glycine soja | 7.0% |
| Radix Glycyrrhiza | 3.0% |
| Rhizoma Rhei | 3.0% |
| Fructus Tritici levis | 5.4% |
| Radix Astragali | 4.0% |
| Radix Rehmannia | 4.0% |
| Fructus Ligustri lucidi | 5.4% |
| Semen Zyziphi spinosae | 3.6% |
| Plumula Nelumbinis | 3.6% |
| Poria Cocos | 3.6% |
| Rhizoma Alismatis | 3.6% |
| Cortex Moutan Radicis | 3% |
| Fructus Corni | 3.6% |
| Radix Achyranthis | 3.6% |
| Concha Ostrea | 4% |
| Radix Asparagi | 4% |
| Radix Pueraria | 3.6% |
| Radix Atractylodis macrocephala | 3.6% |
| Herba Epimedium | 3%. |

6. The method of claim 1, wherein the herbal composition is a unit dose of an extract of a mixture of herbs in amounts per unit dose set forth in the following table:

| Herbal Ingredient | Dry Weight of Herb per Dose (g) |
| --- | --- |
| Herba Scutellaria barbata | 30 g |
| Radix Sophora subprostrata | 30 g |
| Radix Anamarrhena | 12 g |
| Semen Glycine soja | 20 g |
| Radix Glycyrrhiza | 8 g |
| Rhizoma Rhei | 8 g |
| Fructus Tritici levis | 15 g |
| Radix Astragali | 12 g |
| Radix Rehmannia | 12 g |
| Fructus Ligustri lucidi | 15 g |
| Semen Zyziphi spinosae | 10 g |
| Plumula Nelumbinis | 10 g |
| Poria Cocos | 10 g |
| Rhizoma Alismatis | 10 g |
| Cortex Moutan radicis | 8 g |
| Fructus Corni | 10 g |
| Radix Achyranthis | 10 g |
| Concha Ostrea | 12 g |
| Radix Asparagi | 12 g |
| Radix Pueraria | 10 g |
| Radix Atractylodis macrocephala | 10 g |
| Herba Epimedium | 8 g |

7. The method of claim 6, wherein the unit dose is administered on a daily basis.

\* \* \* \* \*